United States Patent [19]

Inami et al.

[11] Patent Number: 4,638,346
[45] Date of Patent: Jan. 20, 1987

[54] FIELD EFFECT TRANSISTOR-TYPE MOISTURE SENSOR

[75] Inventors: Yasuhiko Inami; Masanori Watanabe; Masaya Hijikigawa, all of Nara, Japan

[73] Assignee: Sharp Kabushiki Kaisha, Osaka, Japan

[21] Appl. No.: 763,691

[22] Filed: Aug. 8, 1985

[30] Foreign Application Priority Data

Aug. 29, 1984 [JP] Japan .................................. 59-182088

[51] Int. Cl.⁴ ............................................. G01N 27/12
[52] U.S. Cl. .................................... 357/25; 324/65 R; 324/71.5; 338/35
[58] Field of Search .......................... 357/25; 338/35; 204/430, 1 W; 324/65 R, 71.5

[56] References Cited

U.S. PATENT DOCUMENTS

| | | | |
|---|---|---|---|
| 3,983,527 | 9/1976 | Ohsato et al. | 338/35 |
| 4,397,714 | 8/1983 | Janata et al. | 204/1 T |
| 4,482,581 | 11/1984 | Lorin et al. | 427/79 |
| 4,562,725 | 1/1986 | Oka et al. | 73/29 |

FOREIGN PATENT DOCUMENTS

| | | | |
|---|---|---|---|
| 56-746 | 5/1982 | Japan | 324/71.5 |
| 2145282 | 3/1985 | United Kingdom | 324/65 R |

OTHER PUBLICATIONS

Steven L. Garverick et al, IEEE Trans. on Electron Devices, vol. ED-29, No. 1, pp. 90-94, (Jan. 1982).

*Primary Examiner*—G. L. Kaplan
*Attorney, Agent, or Firm*—Spencer & Frank

[57] ABSTRACT

A field effect transistor-type moisture sensor comprising a field effect transistor device incorporated with a moisture sensitive means, the electrostatic capacity or the electrical conductivity of which varies with the absorption and the desorption of water vapor or moisture, wherein said moisture sensitive means is disposed on a gate insulating film of said field effect transistor device to form an electrode structure, said moisture sensitive means being a film prepared by cross-linking cellulose acetate butyrate with at least one selected from the group consisting of compounds containing two or more isocyanate groups; compounds containing two or more epoxy groups; compounds containing two or more carboxylic acid groups; and acid anhydrides of carboxylic acids.

8 Claims, 4 Drawing Figures

FIELD EFFECT TRANSISTOR-TYPE MOISTURE SENSOR

BACKGROUND OF THE INVENTION

1. Field of the Invention

The present invention relates to a field effect transistor-type moisture sensor for detecting a variation of the gate operation of a field effect transistor due to a variation of humidity, by a moisture sensitive means formed in the vicinity of the gate insulating film of a MOS- or MIS-field effect transistor device. The electric conductivity of the moisture sensitive means varies with the absorption and the desorption of water vapor or moisture.

2. Description of the Prior Art

A field effect transistor (hereinafter, referred to as FET)-type sensor, which comprises an FET device incorporated with a sensitive means exhibiting an electric variation of electrostatic capacity, electric conductivity, electrostatic potential, etc., due to a physical or chemical interaction with the physical quantity to be detected, detects the said physical quantity as a variation of the gate operation of the said FET device. Taking advantage of the high input impedance and the amplifying function of the FET device, such an FET type sensor can exhibit a high output, even though its size is extremely small, and moreover it can be easily adapted to an electronic technology, and thus is advantageous in actual use. Especially, an FET type sensor, which is constructed in such a manner to have a sensitive means in the gate region of the FET device, is advantageous practically and economically since the FET device can be small and a number of devices can be formed on the same substrate. However, such an FET type sensor containing the FET device therein is inferior to an ordinary FET device alone in the operation stability of the FET device. It is also inferior to an FET device in the output stability and the reproducibility of the output characteristic. Depending upon the kind of the FET type sensor required, materials and production processes of the sensitive means are so different that the operation characteristic of the FET device can be remarkably varied. As compared with an ordinary FET device, a large amount of impurities and/or ions are apt to appear in the sensitive means or contamination may occur in the interface between the sensitive means and the gate insulating film during the formation of the sensitive means on the FET device, causing instability not only in the operation characteristic of the FET device but also in the output characteristic of the FET type sensor. Moreover, since the FET type sensor, which is designed to be used as an atmosphere sensor such as a gas sensor, a moisture sensor, etc., is exposed to an atmosphere, it will be contaminated by impurities in the atmosphere, causing variation and/or deterioration of the FET characteristic and/or deterioration of the sensor itself. Accordingly, an FET type sensor must suppress the influence of impurities and/or ions contained in materials of the sensitive means or impurities and/or ions contaminating the interface between the sensitive means and the gate insulating film during the formation of the sensitive means on the FET device and/or during operation of the FET device, thereby providing for a stable output characteristic over a long period of time. If such an FET type sensor is designed, a variety of sensors such as gas sensors, moisture sensors, ion sensors, biological sensors, infrared-ray sensors, etc., will be able to be produced in an FET type format. FET type gas sensors, moisture sensors, ion sensors and biological sensors cannot avoid direct interaction of the sensitive means with the atmosphere so that the device therein cannot be covered with a package, etc. Therefore, the above-mentioned problems deriving from the contamination etc., of impurities and/or ions from the outside must be solved for FET type sensors.

To solve these problems, a silicon nitride film having a small diffusion coefficient concerning ions, moistures, etc., has been used as a gate insulating film, or used to cover the surface of the FET device. The resulting FET sensors are, however, still inferior in the output stability over a long period of time.

In order to solve the above-mentioned problems, the present applicant has proposed an FET type sensor having a double gate-electrode structure which was disclosed in U.S. patent application Ser. No. 697,640 and British Patent Application No. 8503061.

As a moisture sensitive material wherein an electrical resistance or an electrical capacity varies depending upon a variation of humidity or water vapor in the atmosphere, there have been, for example, a moisture sensitive material having a sintered body of metal oxides such as iron oxide ($Fe_2O_3$ or $Fe_3O_4$), tin oxide ($SnO_2$), etc., or a metal oxide film; a moisture sensitive material having a hydrophilic polymer film or a polyelectrolyte; a moisture sensitive material having an electrolyte salt such as lithium chloride (LiCl); and a moisture sensitive material having a hygroscopic resin or polymer film in which conductive particles or fibers such as carbon are dispersed.

While a moisture sensor containing a metal oxide film or a hydrophilic polymer film generally has a wide moisture-sensitivity range, its resistance varies exponentially, responding to relative humidity in the atmosphere. A moisture sensor containing a metal oxide has an excellent heat resistance and responds rapidly, but it has a high temperature resistance coefficient. Especially, moisture sensors having a sintered body of metal oxides are inferior in reproducibility and/or interchangeability of the moisture sensitive characteristics thereof because the moisture sensitive characteristic depends upon the constituents of the sensor to a great extent. A moisture sensor having an electrolyte salt such as lithium chloride detects only humidity in a narrow range and if it is allowed to stand in a highly humid atmosphere for a long period of time, the electrolyte salt therein is eluted or diluted resulting in deterioration of the moisture sensitive characteristic of the sensor, and accordingly it cannot be used for the determination of high humidity. A moisture sensor having a hygroscopic resin or the like, in which conductive particles or fibers are dispersed, cannot detect a humidity in a wide range because it exhibits a steep variation of the resistance thereof in a highly humid atmosphere, while it is not sensitive to low humidity. Also a moisture sensor having a hydrophilic polymer film or a polyelectrolyte film is inferior in humidity resistance, water resistance and durability, while it is advantageous in that it operates in a wide moisture sensitive range, has a rapid moisture sensitive response, a simple structure, and is easily produced at low cost.

In order to solve the above-mentioned problems of the moisture sensitive material, the present applicant has proposed a moisture sensitive material containing a crosslinked cellulose acetate butyrate film which was disclosed in U.S. patent application Ser. No. 707,588.

SUMMARY OF THE INVENTION

The field effect transistor-type moisture sensor of this invention which overcomes the above-discussed and numerous other disadvantages and deficiencies of the prior art, comprises a field effect transistor device incorporated with a moisture sensitive means, the electrostatic capacity or the electrical conductivity of which varies with the absorption and the desorption of water vapor or moisture, wherein said moisture sensitive means is disposed on a gate insulating film of said field effect transistor device to form an electrode structure, said moisture sensitive means being a film prepared by cross-linking cellulose acetate butyrate with at least one selected from the group consisting of compounds containing two or more isocyanate groups; compounds containing two or more epoxy groups; compounds containing two or more carboxylic acid groups; and acid anhydrides of carboxylic acids.

An auxiliary electrode for the application of a drift-cancellation voltage to said moisture sensitive means is, in a preferred embodiment, located at the interface between said gate insulating film and said sensitive means.

The field effect transistor device is, in a preferred embodiment, a MOS- or MIS- field effect transistor device.

Thus, the invention described herein makes possible the objects of (1) providing an FET type moisture sensor wherein an FET device having a double gate-electrode structure is incorporated with a cross-linked cellulose acetate butyrate film as a moisture sensitive material, resulting in the output characteristic thereof ranging from 0 to 100% of the relative humidity, and said output characteristic having a linear relationship with the relative humidity; (2) providing an FET type moisture sensor, the output of which does not bring about a drift; (3) providing an FET type moisture sensor, having a small hysteresis of the moisture sensitive characteristic that is, a difference between the moisture absorption process and the moisture desorption process is small; (4) providing an FET type moisture sensor exhibiting a stable moisture sensitive characteristic even under severe conditions such as a high temperature and highly humid atmosphere; (5) providing an FET type moisture sensor having a rapid response; (6) providing a fine patterned FET type moisture sensor which can be produced by the use of a silicon technology and/or semiconductor processes such as photolithography, plasma etching, etc., thereby attaining a minimization of the size and a reduction of the production cost; and (7) providing an one-chip device in which a signal processing network is incorporated with the FET type moisture sensor mentioned above.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Example 1

Figure 1:
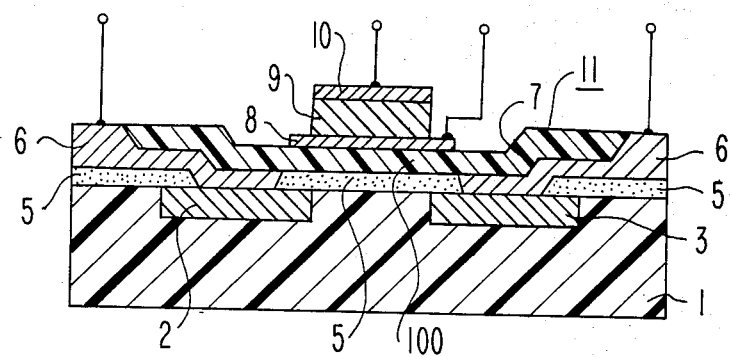
FIG. 1 is a sectional front view showing an FET type moisture sensor according to this invention.

FIG. 1 shows an FET type moisture sensor of this invention, which comprises an FET device 11 incorporated with a moisture sensitive means 9.

The FET device 11 is a MOS-type n-channel FET in which an n-type source 2 and an n-type drain 3 are formed in a row by the diffusion of phosphorus around the surface of a p-type silicon substrate 1. The surface of the silicon substrate 1, is covered with a silicon dioxide film 5 having through-holes for the source 2 and the drain 3. Double layers of the silicon dioxide film ($SiO_2$)5 and a silicon nitride film ($Si_3N_4$)7, on the silicon substrate 1 form between the source 2 and the drain 3, a gate insulating film 100. The silicon nitride film 7 serving to protect the FET device covers a portion of the upper face of each of the conductive electrode films 6, which are formed on the silicon substrate 1 and the silicon dioxide film 5, and which come into contact with the source 2 and the drain 3 at their ends, respectively, which extend through the holes in film 5. On the gate insulating film 100, the moisture sensitive means 9 and a moisture permeable gate electrode film 10 are successively formed. A blocking film 8 made of a conductive film is located between the moisture sensitive means 9 and the silicon nitride film 7. The blocking film 8 serves as an auxiliary electrode which applies a drift-cancellation voltage to the moisture sensitive means 9.

The moisture sensitive means 9 is made as follows: Cellulose acetate butyrate is admixed with an isocyanate compound (e.g., polyisocyanate manufactured by Nippon Polyulethane Kogyo, K.K., Japan) as a cross-linking agent in a ratio of 10 to 1 by weight. The mixture is then dissolved in ethylene glycol monomethyl ether acetate, and the resulting solution is coated on the blocking film 8, which is then air-dried and followed by a heat treatment at a temperature of 100° C. to 200° C. to form a moisture sensitive film, as the moisture sensitive means 9, made of a crosslinked cellulose acetate butyrate film.

The moisture permeable gate electrode film 10 is made of a gold evaporation film having a thickness of about 100 Å, but is not limited thereto. The blocking film 8 is made of a gold or aluminum evaporation film having a thickness of about 2,000 Å, but is not limited thereto. As the FET device, a MIS-type FET can be used.

Figure 2:
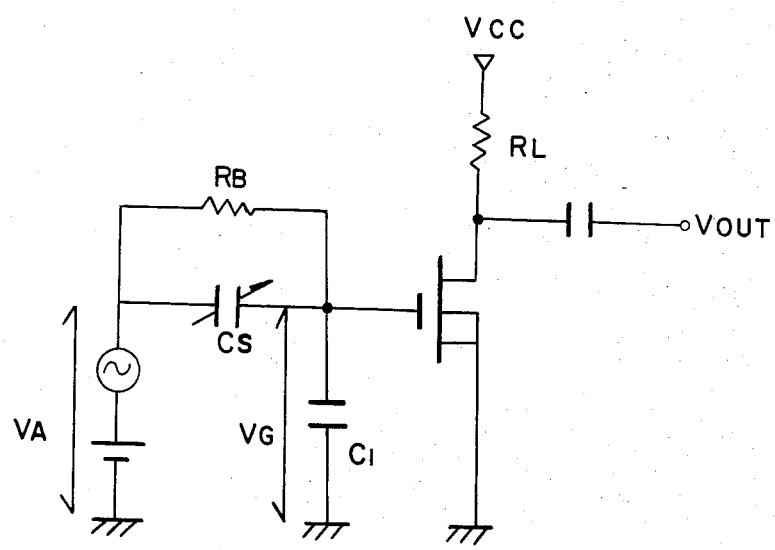
FIG. 2 is an illustration of an equivalent network of the FET type moisture sensor shown in FIG. 1.

FIG. 2 shows an equivalent network of the above-mentioned FET type moisture sensor, wherein references Cs and Ci are electrostatic capacities of the moisture sensitive means 9 and the double layered gate insulating film 100, respectively; reference $R_L$ is a load resistor connected in series with the drain electrode 6; and reference $R_B$ is a resistor connected in series with the blocking film 8.

The basic operation of the FET type moisture sensor according to this invention is explained as follows: In order to simplify the explanation, the case that the moisture sensitive means 9 is directly formed on the gate insulating film 100 without the blocking film 8, that is, the resistor $R_B$ is omitted in the equivalent network in FIG. 2, is described, first.

Given that the voltage to be applied to the moisture permeable gate electrode film 10 is $V_A$ and the threshold voltage of the FET device 11 is $V_{th}$, the drain current $I_D$ can be represented by the following equation (1):

$$I_D = \frac{\beta}{2}(V_A - V_{th})^2, \beta = \frac{\mu n C W}{L} \quad (1)$$

wherein $\mu n$ is a carrier mobility; L and W are the channel length and the channel width of the FET device, respectively; C is an electrostatic capacity, in the case where an electrostatic capacity Ci of the gate insulating film is connected in series with an electrostatic capacity $C_s$ of the moisture sensitive means 9, and being represented by the equation (2):

$$C = \frac{C_s C_i}{C_s + C_i} \quad (2)$$

Thus, given that $V_A$ is a constant value, moisture can be detected as a variation of the drain current $I_D$ with the variation of the electrostatic capacity $C_s$ of the moisture sensitive means 9 depending upon the moisture of the external atmosphere.

Since a DC potential difference exists between both surfaces of the moisture sensitive means 9, impurities and/or ions contained in the moisture sensitive means 9 migrate by the action of an electric field, thereby attaining a rearrangement and/or a localization thereof which have a remarkable effect on the device characteristic in the channel region of the FET device, causing a variation of the threshold voltage $V_{th}$ and the drift of the operation characteristic of the FET device, and further causing a drift of the output signal as a moisture sensor. In the case where impurities and/or ions are contained in the interface between the moisture sensitive means 9 and the moisture permeable gate electrode film 10 and/or the interface between the moisture sensitive means 9 and the gate insulating film 100, the same phenomenon as the above-mentioned occurs as well. As described above, the contamination by impurities and/or ions from the external atmosphere into the device is unavoidable, and accordingly the solution of such problems is of great importance in providing the desired FET type moisture sensor.

In order to solve such problems and thereby provide an FET type moisture sensor which can operate stably over a long period of time, an FET type moisture sensor according to this invention comprises a conductive blocking film 8 located between the moisture sensitive means 9 and the gate insulating film 100, as shown in FIG. 1. The blocking film 8 is connected with the moisture permeable gate electrode film 10 on the moisture sensitive means 9 by the resistor $R_B$ as shown in FIG. 2. A voltage $V_A$, which is composed of a DC voltage $V_A$ (DC) and an AC voltage $V_A$ (AC) of frequency f superposed thereon, is applied to the gate insulating film 100 and the moisture sensitive means 9 through the moisture permeable gate electrode film 10 and the blocking film 8 to thereby drive this FET type moisture sensor. In the case where the DC voltage $V_A$ (DC) is smaller than the withstand voltage of the gate insulating film 100 and a leakage current does not occur through the gate insulating film 100, the DC voltage component $V_G$(DC) of the effective gate voltage $V_G$ applied to the blocking film 8 becomes equal to the DC voltage $V_A$ (DC), resulting in no DC potential difference between both surfaces of the moisture sensitive means 9, so that the above-mentioned phenomenon, that impurities and/or ions migrate within the moisture sensitive means 9 causing their rearrangement and/or localization, can be suppressed and, additionally, the diffusion of these impurities and/or ions into the gate insulating film 100 can be suppressed because of the incorporation of the blocking film 8. Since the DC voltage $V_G$ (DC) is equal to the DC voltage $V_A$ (DC), this FET type moisture sensor cannot, of course, operate as a moisture sensor by the application of the DC voltage $V_A$ (DC) alone. The DC voltage $V_A$ (DC) functions to give an optimum bias voltage in the $I_D$-$V_G$ characteristic of the FET device.

In order that the FET type moisture sensor operates as a moisture sensor, that is, it detects the variation of an electrostatic capacity $C_s$ of the moisture sensitive means due to moisture in an atmosphere, an AC voltage $V_A$ (AC) is essential.

In the case where the resistor $R_B$, having a resistance value which is sufficiently great as compared with the impedance $(2 f C_S)^{-1}$ of the moisture sensitive means at frequency f, is connected to the block film 8 and the moisture permeable gate electrode film 10, the resistance of the $R_B$ is negligible and the AC voltage component $V_G$(AC) of the gate voltage $V_G$ can be represented by the equation (3):

$$V_G(AC) = \frac{C_s}{C_s + C_i} V_A(AC) \quad (3)$$

This indicates that since $V_G$ (AC) varies with the values of an electrostatic capacity $C_s$ of the moisture sensitive means at the application of $V_A$ (AC) with a given amplitude, the output signal required for a moisture sensor can be detected as the AC amplitude of the drain current $I_D$.

Figure 3:
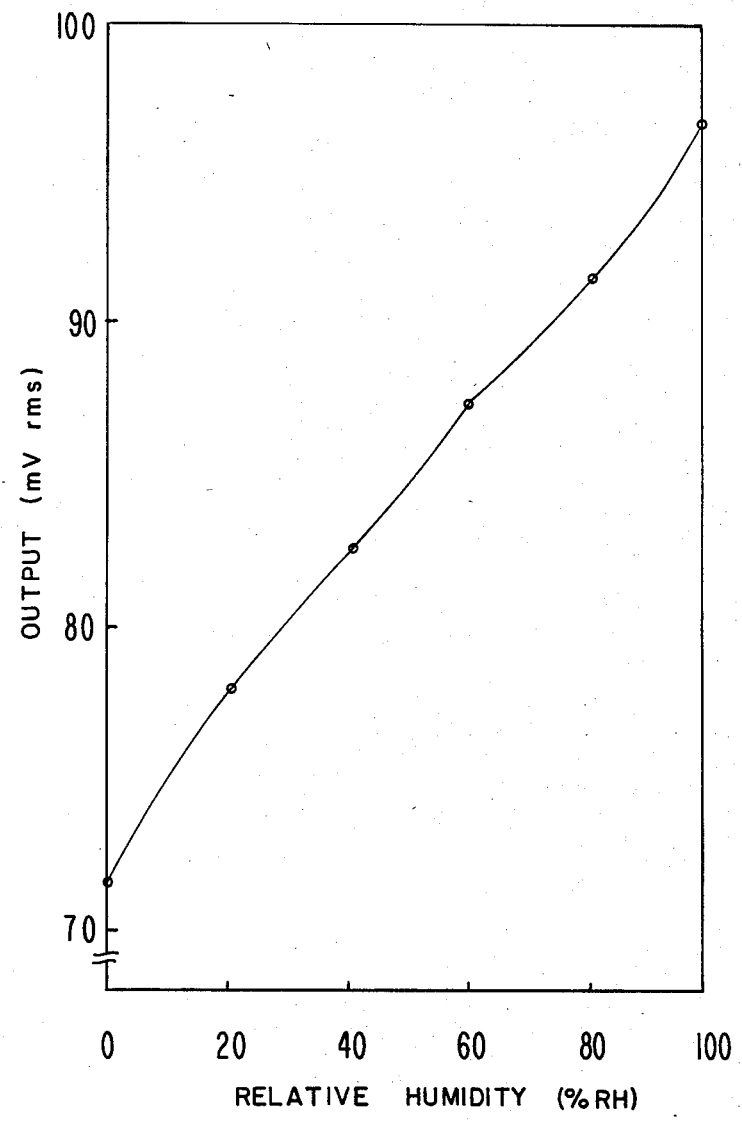
FIG. 3 shows a characteristic curve showing the relationship between the output and the relative humidity of the moisture sensor in FIG. 1.

FIG. 3 shows the output—the relative humidity characteristic experimentally measured while the above-mentioned FET type moisture sensor operated under the conditions that the values of the fixed resistors $R_B$ and $R_L$, respectively, are 10 M$\Omega$ and 1 K$\Omega$; $V_A$ (DC) is 5 V; and $V_A$ (AC) is 100 mV rms (10 KHz).

Figure 4:
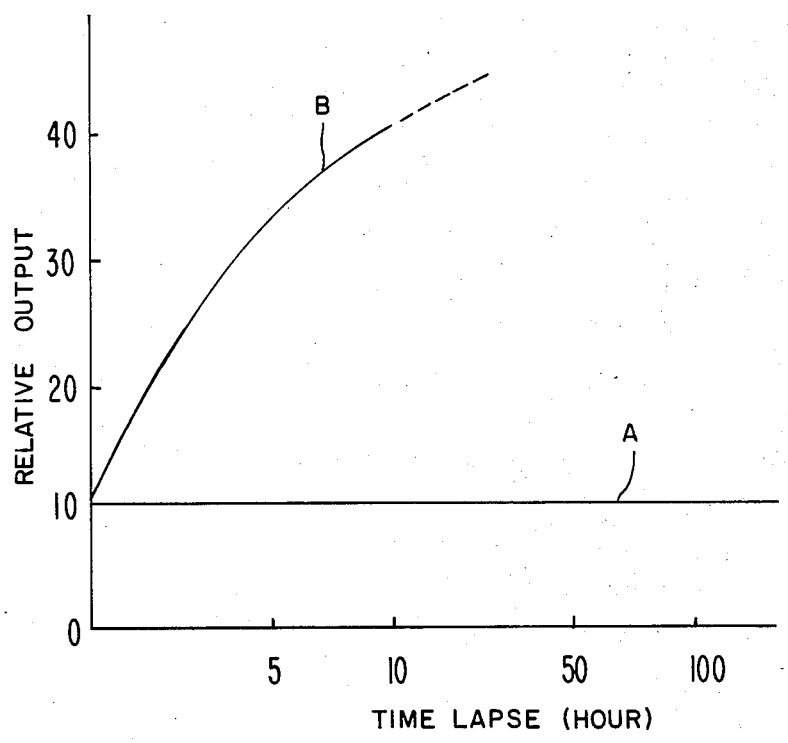
FIG. 4 shows characteristic curves, one curve (A) of which shows the drift of the experimental output value of the FET type moisture sensor in FIG. 1 and the other (B) of which shows the drift of the experimental output value of a control FET type moisture sensor containing no blocking film.

In order to reveal the output stability of the above-mentioned FET type moisture sensor, the relationship between the time for which the FET device was allowed to stand in an atmosphere having a relative humidity of 60% and the output of the FET type moisture sensor was examined and is shown in FIG. 4, wherein the characteristic curve A shows the drift of the output of the test sensor containing the blocking film 8 while the characteristic curve B shows the drift of the output of the control sensor containing no blocking film 8. Both sensors were subjected to examination under the same operating and measuring conditions, and their outputs, respectively, were expressed by a relative value on the basis of the initial output value. FIG. 4 indicates that the use of the blocking film 8 is significantly effective to maintain the output of the FET type moisture sensor stably for a long period of time and that the drain current ($I_D$)—the drain voltage ($V_{DS}$) characteristic, the drain current ($I_D$)—the gate voltage ($V_G$)

characteristic, etc., of the FET device are stable, do not drift and exhibit excellent reproducibility. On the contrary, in the case where the blocking film 8 is not employed as shown by the characteristic curve B in FIG. 4, both the $I_D$-$V_{DS}$ characteristic and the $I_D$-$V_G$ characteristic of the FET device exhibit great drift and are extremely inferior in reproducibility. Moreover, it can be observed that the $I_D$-$V_{DS}$ characteristic and/or the $I_D$-$V_G$ characteristic are greatly different from the initial characteristic even when the ON-OFF operation or the polarity at the application of $V_G$ is reversed. This phenomenon indicates that the migration and the redistribution (rearrangement) of impurities and/or ions in the moisture sensitive means and/or the interface between the moisture sensitive means and the gate insulating film by the action of an electric field have a remarkable effect on the characteristics of the FET device.

In order to examine resistance to a severe environment of the FET type moisture sensor, the sensor was allowed to stand in a high temperature and highly humid atmosphere (e.g., a temperature of 60° C. and a relative humidity of 90–95%) over 1,000 hours or more. The moisture sensitive characteristic thereof did not vary.

Example 2

The moisture sensitive means 9 was made as follows: Cellulose acetate butyrate was admixed with dicarboxylic acid as a crosslinking agent (e.g., terephthalic acid) in a ratio of 5 to 2 by weight. The mixture was dissolved in a dimethyl sulfoxide solution with an adequate viscosity, and the resulting solution was coated on the blocking film 8, which was then air-dried and followed by a heat treatment at a temperature of 100° C. to 200° C. to form a crosslinked film as the moisture sensitive means. Using the resulting film, an FET type moisture sensor was produced in the same manner as in Example 1. The moisture sensitive characteristic of the FET type moisture sensor was examined, in the same manner as in Example 1, indicating that a linear relationship exists between the output characteristic and the relative humidity in the whole range of 0% to 100% of the relative humidity. Even if the FET type moisture sensor was allowed to stand in a high temperature and highly humid atmosphere (60° C., 90–95% relative humidity) over 1,000 hours, the moisture sensor was treated with organic chemicals, confirming that the moisture sensitive characteristic of the sensor did not vary.

Example 3

The moisture sensitive means 9 was made as follows: Cellulose acetate butyrate was admixed with an epoxy compound (e.g., 1.3-butadienediepoxide or 1.7-octadienediepoxide, both of which were manufactured by Tokyo Kasei Kogyo K.K., Japan) as a crosslinking agent in the ratio of 5 to 2 by weight. The mixture was then dissolved in a dimethyl sulfoxide solution with an adequate viscosity, and the resulting solution was coated on the blocking film 8, which was then air-dried and followed by a heat treatment at a temperature of 100° C. to 200° C. to form a crosslinked film as the moisture sensitive means 9. Using the resulting film, a FET type moisture sensor was produced in the same manner as in Example 1. The FET type moisture sensor was then subjected to the same tests as in Examples 1 and 2 which gave the same excellent results as in Examples 1 and 2.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A field effect transistor-type moisture sensor comprising a field effect transistor device incorporated with a moisture sensitive means, the electrostatic capacity or the electrical conductivity of which varies with the absorption and the desorption of water vapor or moisture, wherein said moisture sensitive means is disposed on a double-layered gate insulating film of said field effect transistor device, a gate electrode is connected to said moisture sensitive means, an auxiliary electrode for the application of a drift-cancellation voltage to said moisture sensitive means is located at the interface between said gate insulating film and said sensitive means, and said moisture sensitive means is a film prepared by cross-linking cellulose acetate butyrate with at least one compound selected from the group consisting of compounds containing two or more isocyanate groups, compounds containing two or more epoxy groups, compounds containing two or more carboxylic acid groups, and acid anhydrides of carboxylic acids.

2. A field effect transistor-type moisture sensor according to claim 1, wherein said field effect transistor device is a MOS- or MIS-field effect transistor device.

3. A field effect transistor-type moisture sensor according to claim 1, wherein said gate insulating film comprises double layers of a silicon dioxide film and a silicon nitride film.

4. A MIS-field effect transistor type moisture sensor comprising a field effect transistor device incorporated with a moisture sensitive means, the electrostatic capacity or the electrical conductivity of which varies with the absorption and the desorption of water vapor or moisture, wherein said moisture sensitive means is disposed on a gate insulating film of said field effect transistor device, a gate electrode for the field effect transistor is disposed on the outer surface of said moisture sensitive means, an auxiliary electrode for the application of a drift-cancellation voltage to said moisture sensitive means is located at the interface between said gate insulating film and said moisture sensitive means, and said moisture sensitive means is a film prepared by cross-linking cellulose acetate butyrate with at least one compound selected from the group consisting of compounds containing two or more isocyanate groups, compounds containing two or more epoxy groups, compounds containing two or more carboxylic acid groups, and acid anhydrides of carboxylic acids.

5. A field effect transistor-type moisture sensor comprising in combination: a silicon semi-conductor body having spaced source and drain regions formed therein adjacent one surface to define a channel region therebetween; source and drain electrodes for said source and drain regions, respectively; an insulating layer covering said surface; a moisture sensitive film, the electro static capacity of the electrical conductivity of which varies with the absorption and the desorption of water vapor or moisture, disposed on said insulating layer over said channel region, said moisture sensitive film being prepared by cross-linking cellulose acetate butyrate with at least one compound selected from the group consisting of compounds containing two or more isocyanate groups, compounds containing two or more epoxy groups, compounds containing two or more carboxylic acid groups, and acid anhydrides of carboxylic acids; means, including an auxiliary electrode located at the interface between said insulating layer and said moisture sensitive film, for applying a drift-cancellation voltage to said moisture sensitive film; and a gate electrode disposed on the outer surface of said moisture sensitive film.

6. A field effect transistor as defined in claim 5 wherein said insulating layer includes a first layer of an insulating material disposed on said surface of said semiconductor body and an overlying layer of a different insulating material.

7. A field effect transistor as defined in claim 6 wherein said first layer of insulating material is silicon dioxide and said overlying layer is silicon nitride.

8. A field effect transistor-type moisture sensor according to claim 1, 4, 5, 6 or 7 wherein said moisture sensitive means has a linear output characteristic in the range from 0% to 100% of the relative humidity.

* * * * *